(12) United States Patent
Uda et al.

(10) Patent No.: US 9,125,769 B2
(45) Date of Patent: Sep. 8, 2015

(54) ABSORBENT ARTICLE

(75) Inventors: Masashi Uda, Kagawa (JP); Toru Oba, Kagawa (JP); Satoshi Mizutani, Kagawa (JP)

(73) Assignee: Unicharm Corporation, Ehime (JP)

( * ) Notice: Subject to any disclaimer, the term of this patent is extended or adjusted under 35 U.S.C. 154(b) by 381 days.

(21) Appl. No.: 13/637,824

(22) PCT Filed: Mar. 17, 2011

(86) PCT No.: PCT/JP2011/057268
§ 371 (c)(1),
(2), (4) Date: Sep. 27, 2012

(87) PCT Pub. No.: WO2011/125530
PCT Pub. Date: Oct. 13, 2011

(65) Prior Publication Data
US 2013/0012900 A1    Jan. 10, 2013

(30) Foreign Application Priority Data

Mar. 31, 2010   (JP) ................................ 2010-082893

(51) Int. Cl.
*A61F 13/15*    (2006.01)
*A61F 13/84*    (2006.01)

(52) U.S. Cl.
CPC ....... *A61F 13/15* (2013.01); *A61F 2013/15243* (2013.01); *A61F 2013/8497* (2013.01)

(58) Field of Classification Search
CPC .............. A61F 2013/15243; A61F 2013/8497; A61F 13/42; A61F 13/15; A61F 13/47

USPC ................................................... 604/358, 361
See application file for complete search history.

(56) References Cited

U.S. PATENT DOCUMENTS

| | | | | |
|---|---|---|---|---|
| 3,860,003 | A | * | 1/1975 | Buell ..................... 604/385.25 |
| 4,623,340 | A | | 11/1986 | Luceri |
| 5,190,563 | A | * | 3/1993 | Herron et al. ..................... 8/120 |
| 2003/0109839 | A1 | | 6/2003 | Cpstea et al. |
| 2003/0114818 | A1 | | 6/2003 | Benecke et al. |

(Continued)

FOREIGN PATENT DOCUMENTS

| EP | 1 108 406 A2 | 6/2001 |
|---|---|---|
| EP | 1 818 032 A1 | 8/2007 |

(Continued)

OTHER PUBLICATIONS

International Search Report based on PCT application No. PCT/JP2011/057268 dated May 24, 2011 (6 pgs).

(Continued)

*Primary Examiner* — Lynne Anderson
*Assistant Examiner* — Bradley Philips
(74) *Attorney, Agent, or Firm* — Brinks Gilson & Lione

(57) ABSTRACT

An absorbent article that includes an absorber capable of absorbing a body fluid of a user, a liquid-permeable sheet covering one surface of the absorber and allowing a body fluid of the user to pass through, and a liquid-impermeable sheet covering another surface of the absorber and disallowing a body fluid of the user to pass through, wherein the color of the liquid-permeable sheet has an L* value of 88 or more, an a* value of 0 to 0.3 and a b* value of −8 to 0 in the L*a*b* color system, and the color of the absorber has a b* value of 1 to 5 and an L* value of 93 or more in the L*a*b* color system.

20 Claims, 1 Drawing Sheet

(56) References Cited

U.S. PATENT DOCUMENTS

| | | |
|---|---|---|
| 2003/0135174 A1 | 7/2003 | Benecke et al. |
| 2003/0208859 A1 | 11/2003 | Neogi et al. |
| 2005/0217810 A1* | 10/2005 | Stoyanov et al. ............ 162/9 |
| 2006/0021536 A1 | 2/2006 | Song et al. |
| 2011/0144610 A1* | 6/2011 | Karlson et al. ............ 604/372 |

FOREIGN PATENT DOCUMENTS

| | | |
|---|---|---|
| JP | 5-24783 B2 | 4/1993 |
| JP | 2001-258936 A | 9/2001 |
| JP | 2004-3098 A | 1/2004 |
| JP | 2004-504106 A | 2/2004 |
| JP | 2005-511339 A | 4/2005 |
| JP | 2005-290655 A | 10/2005 |
| JP | 2006-181294 A | 7/2006 |
| JP | 4050536 B2 | 12/2007 |
| JP | 2008-93290 A | 4/2008 |
| JP | 2009-207684 A | 9/2009 |
| JP | 2009-291473 A | 12/2009 |
| JP | 2010-24573 A | 2/2010 |
| JP | 2 248 497 A1 | 11/2010 |

OTHER PUBLICATIONS

European extended Search Report from corresponding European application No. 11765431.9 dated Apr. 22, 2014 (6 pgs).

Japanese Office Action from corresponding Japanese Application No. 2010-082893 dated Feb. 28, 2014 (2 pgs).

\* cited by examiner

ABSORBENT ARTICLE

RELATED APPLICATION

This application is a 35 U.S.C. §371 national phase filing of International Patent Application No. PCT/JP2010/057268, filed Mar. 17, 2011, through which and to which priority is claimed under 35 U.S.C. §119 to Japanese Patent Application No. 2010-082893, filed Mar. 31, 2010.

TECHNICAL FIELD

The present invention relates to an absorbent article having a liquid-permeable sheet covering an absorber.

BACKGROUND ART

An absorbent article, such as a diaper or sanitary napkin has a surface material on the surface coming into contact with skin so that a user can feel good when the surface material comes into contact with the user's skin. An absorbent article where the surface material is composed of an upper layer and a lower layer and the lower layer is colored to make the color of the lower layer visible when the surface material is viewed from the upper layer side, wherein a color of the colored lower layer has a b* value of 5 or more in the L*a*b* color system, is known as a conventional technique (see, for example, Patent Document 1). The color of the lower layer improves the absorbent article's appearance. Also, when menstrual blood or vaginal discharge remains in the surface material, the color of the colored lower layer can make the color of the menstrual blood or vaginal discharge less-visible. Furthermore, the color of the menstrual blood or vaginal discharge absorbed by the absorber can be effectively concealed by the color of the colored lower layer.

RELATED ART

Patent Document

[Patent Document 1] Kokai (Japanese Unexamined Patent Publication) No. 2006-181294

SUMMARY OF THE INVENTION

Problems to be Solved by the Invention

The color of the absorber generally has a b* value of 1 to 12 in the L*a*b* color system (see Table 2 showing the L*a*b* color systems of representative absorbers) and is tinged with yellow. The color of the lower layer of the surface material described in Patent Document 1 has a b* value of 5 or more, and therefore is also tinged with yellow. Since both the absorber and the surface material are tinged with yellow, the absorber in being viewed through the surface material looks more yellowish than the absorber in being viewed directly. The user may feel the absorbent article dirty due to the yellowish absorber when wearing the absorbent article.

Means to Solve the Problems

The present invention employs the following configurations so as to solve the problems. The absorbent article of the present invention comprises an absorber capable of absorbing a body fluid of a user, a liquid-permeable sheet covering one surface of the absorber and allowing body fluid of the user to pass through, and a liquid-impermeable sheet covering another surface of the absorber and disallowing body fluid of the user to pass through, wherein the color of the liquid-permeable sheet has an L* value of 88 or more, an a* value of 0 to 0.3 and a b* value of −8 to 0 in the L*a*b* color system, and the color of the absorber has a b* value of 1 to 5 and an L* value of 93 or more in the L*a*b* color system. According to the invention, the absorber can be prevented from looking yellow-tinged and at the same time, appearing darkened. When an absorber having a b* value of more than 5 and an L* value of less than 93 is covered with the liquid-permeable sheet, the absorber may be prevented from looking yellow-tinged (specifically, the b* value is 1 or less) but looks darkish (specifically, the L* value is less than 88), or the absorber may not look darkish (specifically, the L* value is 88 or more) but looks yellow-tinged (specifically, the b* value is 1 or less; when the later-described Nonwoven Fabric B or C and Absorber E or F are combined). For this reason, an absorber having a b* value of 7 or more and an L* value of less than 93 is not included in the present invention. In the absorbent article above, when the absorber is viewed through the liquid-permeable sheet, the L* value of the color of the absorber is 88 or more. Also, when the absorber is viewed through the liquid-permeable sheet, the a* value of the color of the absorber is from −1 to 0.2 and the b* value is from −8 to 1. The liquid-permeable sheet is preferably a surface material coming into contact with skin of the user or an intermediate sheet present between the surface material and the absorber. Furthermore, the light transmittance of the liquid-permeable sheet is from 30 to 70%. If the light transmittance of the nonwoven fabric is less than 30%, the tint of the absorber may be made invisible but the liquid permeability of the nonwoven fabric becomes bad, whereas if it exceeds 70%, the effect of blue color of the surface material 2 is not sufficiently exerted. The color of the liquid-permeable sheet is light blue, and the weight ratio of the colorant for coloring the liquid-permeable sheet in blue is from 500 to 3,000 ppm based on the permeable sheet.

Effects of the Invention

According to the present invention, a liquid-permeable sheet having an L* value of 88 or more, an a* value of 0 to 0.3 and a b* value of −8 to 0 in the L*a*b* color system is disposed to cover an absorber having a b* value of 1 to 5 and an L* value of 93 or more in the L*a*b* color system, so that the absorber viewed through the liquid-permeable sheet can result in a b* value of −8 to 1 and an L* value of 88 or less. According to the invention, when the user views a yellow-tinged absorber through the liquid-permeable sheet, the absorber does not look yellow-tinged and is not darkened, and therefore the absorbent article looks clean.

BEST MODE FOR CARRYING OUT THE INVENTION

Figure 1:
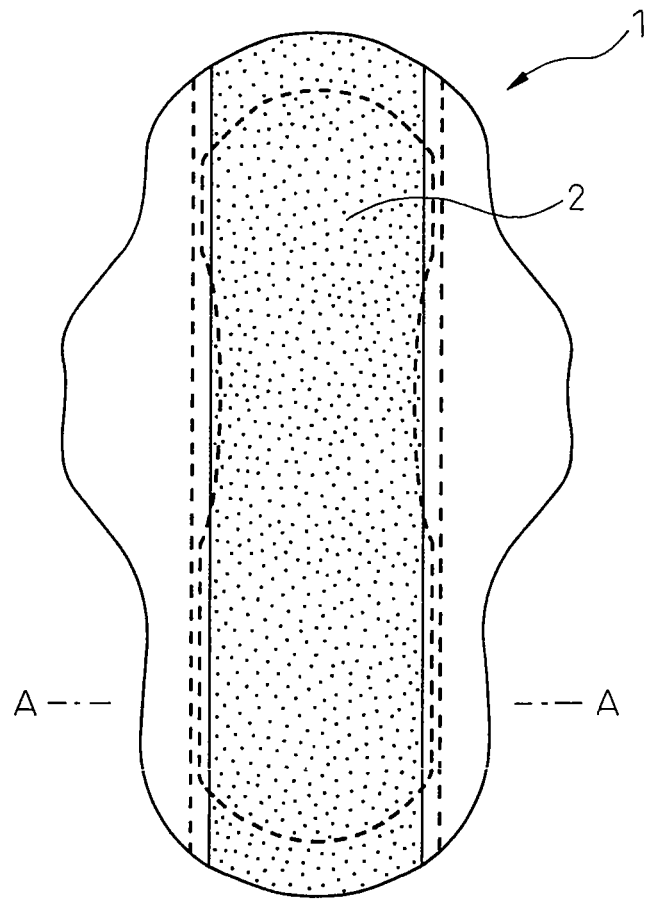
FIG. 1 is a front view of the sanitary napkin in one embodiment of the present invention.
Figure 2:
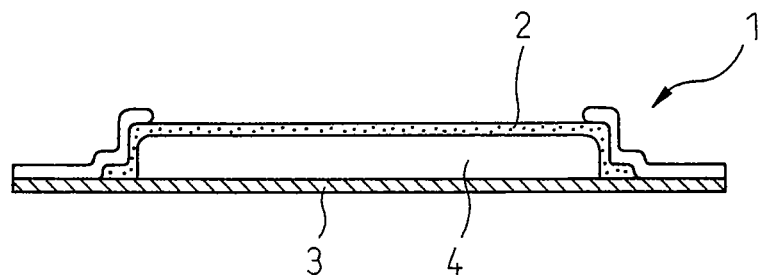
FIG. 2 is an A-A cross-sectional view of the sanitary napkin of FIG. 1.

The absorbent article of the present invention is described below by referring to, for example, a sanitary napkin that is an absorbent article in one embodiment. FIG. 1 is a plan view of the sanitary napkin 1 as an example in one embodiment of the present invention, and FIG. 2 is an A-A cross-sectional view of the sanitary napkin 1 of FIG. 1. As illustrated in FIGS. 1 and 2, the sanitary napkin 1 comprises a liquid-permeable surface material 2, a liquid-impermeable leakage-preventive sheet 3 and an absorber 4 disposed between the surface material 2 and the leakage-preventive sheet 3.

Details of the surface material 2 are described later, and the leakage-preventive sheet 3 is first described. The leakage-preventive sheet 3 is a liquid-impermeable sheet disallowing a body fluid to pass through and is provided so as to prevent the discharged body fluid from leaking to the outside. The material for the leakage-preventive sheet 3 is not particularly limited as long as it is a material disallowing the discharged body fluid to pass through. For example, a waterproof-treated nonwoven fabric, a plastic film composed of polyethylene or the like, or a composite material of nonwoven fabric and plastic film can be used for the leakage-preventive sheet 3.

The absorber 4 absorbs and holds the discharged body fluid. The material for the absorber 4 is not particularly limited as long as it is a material capable of absorbing the discharged body fluid. Examples of the absorber include an absorber composed of a fluffed pulp or an air-laid nonwoven fabric and a super-absorbent polymer. Other examples include, instead of using a fluffed pulp, a fiber network absorber using a chemical pulp, a cellulose fiber, an artificial cellulose fiber, such as rayon and acetate, or a synthetic fiber (including a composite fiber) such as polyolefin, polyester and polyamide, and a foam absorber using a foam material such as polyurethane. Examples of the air-laid nonwoven fabric include a nonwoven fabric in which pulp and a synthetic fiber are thermally fused or bonded by a binder. The super-absorbent polymer (SAP) has a three-dimensional network structure in which a water-soluble polymer is appropriately crosslinked, which can absorb water whose volume is hundreds to thousands of times the volume of the polymer, but is substantially water-insoluble and does not release the once absorbed water even when some pressure is applied. Examples thereof include starch-based, acrylic acid-based and amino acid-based particulate or fibrous polymers. The shape and structure of the absorber may be changed as needed, and the total absorption amount of the absorber is designed depending on the absorption amount of an absorbent article and the usage of the absorbent article. Also, the size, absorption capacity and the like of the absorber 4 are varied according to the usage. The color of the absorber 4 is generally a yellow-tinged white color or a light yellow color, and the color of the absorber 4 has a b* value of 1 to 12 and an L* value of 90 or more in the L*a*b* color system (the color systems of representative absorbers are shown in Table 2).

The surface material 2 is described in detail below. The surface material 2 is a liquid-permeable sheet allowing a body fluid to pass through and is provided on the surface coming into contact with skin of the user so as to improve the feeling of touch on the skin when the user wears the sanitary napkin 1. Accordingly, the surface material 2 preferably has a function of providing the user with good feel when the user's skin touches the sanitary napkin 1. For example, the surface material 2 is produced by using a fine fiber and has a smooth surface and flexibility. The surface material 2 is slightly colored light blue, and the absorber 4 is visible through the surface material 2.

For the surface material 2, a nonwoven fabric is generally used, and this fabric can be formed by a well-known air-through method using a card web. The production method of the nonwoven fabric used for the surface material 2 is not limited to the above-described air-through method, and examples of the method which may be used for the production of a nonwoven fabric include a needle punching or spunlacing system of entangling a fiber web to form a stable sheet, a binder bonding or thermal bonding system of fixing fibers by means of an adhesive or fixing a web by the melting of the fiber itself, a spunbonding system of forming filament fibers into a seal, and a wet method of forming a sheet by papermaking.

The fiber for use in the nonwoven fabric of the surface material 2 is composed of, for example, linear low-density polyethylene (LLDPE), low-density polyethylene (LDPE), medium-density polyethylene (MDPE), high-density polyethylene (HDPE), polypropylene, polybutylene, a copolymer based on the polymer above, such as ethylene-vinyl acetate copolymer (EVA), ethylene-ethyl acrylate copolymer (EEA) and ethylene-acrylic acid copolymer (EAA), a polyolefin-based polymer such as ionomer resin, a polyester-based polymer, such as polyethylene terephthalate (PET), polybutylene terephthalate (PBT), polytrimethylene terephthalate (PTT) and polylactic acid, or a polyamide-based polymer such as nylon.

The fiber for the nonwoven fabric of the surface material 2 need not be composed of a single component and may be a composite fiber, such as core-sheath type fiber, side-by-side type fiber and island/sea type fiber. Above all, a composite fiber composed of a core part and a sheath part is preferred in consideration of thermal bonding. The cross-sectional shape of the fiber for the nonwoven fabric is not limited to a circular shape but may be a heteromorphic shape such as triangular, square or star-like shape. Furthermore, the core portion of the fiber for the nonwoven fabric may be hollow, or the fiber for the nonwoven fabric may be porous. The cross-sectional area ratio between the core part and the sheath part in the core/sheath structure of the fiber for the nonwoven fabric is not particularly limited but is preferably from 80/20 to 20/80, more preferably from 60/40 to 40/60. If the cross-sectional area ratio between the core part and the sheath part in the core/sheath structure of the fiber for the nonwoven fabric exceeds 80/20 in terms of the cross-sectional area of the core part, bonding between fibers sometimes becomes weak, whereas if the cross-sectional area ratio between the core part and the sheath part in the core/sheath structure of the fiber for the nonwoven fabric exceeds 20/80 in terms of the cross-sectional area of the sheath part, a large part of the fiber is sometimes fused in the step of thermal bonding between fibers.

The fineness of the fiber used for the nonwoven fabric of the surface material 2 is preferably from 1.0 to 20 dtex and as the surface material of the adsorbent article, the fineness is more preferably from 1.2 to 4.4 dtex. Also, the fiber length of the fiber used for the nonwoven fabric of the surface material 2 is preferably from 5 to 75 mm and in consideration of card suitability, the fiber length is more preferably from 25 to 51 mm.

The basis weight of the fiber used for the nonwoven fabric of the surface material 2 is preferably from 10 to 100 g/m$^2$ and in consideration of a so-called rewet back phenomenon where the liquid absorbed by the absorbent layer leaks out to the surface side, light permeability and the like, the basis weight is more preferably from 20 to 35 g/m$^2$. The density of the fiber used for the nonwoven fabric of the surface material 2 is preferably from 0.001 to 0.2 g/cm$^3$ and in consideration of rewet back, liquid permeability and the like, the density is more preferably from 0.015 to 0.08 g/cm$^3$. The thickness of the nonwoven fabric of the surface material 2 under a weight of 3 g/cm$^2$ is preferably from 0.1 to 3 mm and in consideration of rewet back and liquid permeability, the thickness is more preferably from 0.5 to 2 mm.

As described above, the surface material 2 is colored light blue, and the color of the surface material 2 is described below. The color of the surface material 2 is preferably light blue, more specifically, preferably has an L* value of 88 or more, an a* value of 0 to 0.3 and a b* value of −8 to 0 in the L*a*b* color system.

If the L* value is less than 88, the blue color of the surface material 2 becomes too dark and the absorber 4 viewed through the surface material 2 sometimes looks darkish. Also, if the a* value is less than 0, the color of the surface material 2 becomes greenish, whereas if it exceeds 0.3, the color of the surface material 2 becomes purplish. In both cases, the clean feeling of the absorber 4 viewed through the surface material 2 is sometimes deteriorated. Furthermore, if the b* value is less than −8, the blue color of the surface material 2 becomes too deep and the color of the absorber 4 viewed through the surface member 2 sometimes looks darkish, whereas if the b* value exceeds 0, the color of the surface material 2 is tinged with yellow and when the absorber 4 is viewed trough the surface material 2, the yellow tint of the absorber 4 is reinforced.

In the L*a*b* color system, L* indicates the brightness of the color and a*b* indicates the tint of the color. When the L* value increases, the color becomes brighter and at the same time, becomes whitish, and when the L* value decreases, the color becomes darker and blackish. When the a* value increases, the tint shifts to the red direction, and when the a* value decreases, the tint shifts to the green direction. When the b* value is changed in the plus direction, the tint shifts to the yellow direction, and when the b* value is changed in the minus direction, the tint shifts to the blue direction.

Coloring of the surface material 2 is described below. The surface material 2 is a colored nonwoven fabric, and the method for obtaining a colored nonwoven fabric include a method of performing coloring at the production of the nonwoven fabric and a method of coloring the nonwoven fabric as a post-step.

The method of performing coloring at the production of the nonwoven fabric include a method utilizing a colored fiber and a method utilizing a colored binder. In the method utilizing a colored fiber, the colored nonwoven fabric is produced using a short fiber colored with a pigment. The nonwoven fabric produced by this method is good in the dye fastness. In the method utilizing a colored binder, the binder used for bonding short fibers to each other at the production of the nonwoven fabric is colored with a pigment, whereby a colored nonwoven fabric can be produced. According to this method, the nonwoven fabric can be colored without any effect of the kind of the constituent fiber. The nonwoven fabric can also be colored by combining the method utilizing a colored fiber and the method utilizing a colored binder.

The method of coloring the nonwoven fabric as a post-step includes a dyeing method using a colored binder and a dyeing method using a colorant. In the dyeing method using a colored binder, the nonwoven fabric to be colored is impregnated with a colored binder and after squeezing and drying the impregnated nonwoven fabric, the colored binder impregnating the nonwoven fabric is cured, whereby the nonwoven fabric can be colored. According to this method, the nonwoven fabric can be colored irrespective of the constituent fiber of the nonwoven fabric. The nonwoven fabric may also be colored by printing the colored binder by a printing system. In the dyeing method using a colorant, the nonwoven fabric is colored by saturating the nonwoven fabric with a colorant. The colorant used for coloring of the nonwoven fabric is determined by the constituent fiber of the nonwoven fabric, and the colorant selected for use in coloring the nonwoven fabric is, for example, a dispersive dye in the case of a polyester fiber and an acidic dye, a metal complex salt dye or a dispersive dye in the case of a nylon fiber. Dyeing of the nonwoven fabric is generally performed by impregnating the nonwoven fabric with a colorant, drying the nonwoven fabric, curing the dye impregnating the nonwoven fabric and after water washing, again drying the nonwoven fabric.

When the nonwoven fabric is colored by using a colored binder, the colored binder sometimes makes the texture of the nonwoven fabric harden, and therefore the nonwoven fabric using the surface material 2 is preferably colored by a method utilizing a colored fiber or a dyeing method using a colorant.

The pigment for coloring the fiber used in the method utilizing a colored fiber is not particularly limited as long as the fiber can be colored blue, but preferred examples thereof include an inorganic blue pigment, such as Pigment Blue 27, Pigment Blue 28 and Pigment Blue 29, and an organic blue pigment such as Pigment Blue 15, Pigment Blue 16, Pigment Blue 60 and Phthalocyanine Blue α. The weight ratio of the pigment to the entire nonwoven fabric is preferably from 500 to 3,000 ppm. If the weight ratio of the pigment is less than 500 ppm, the blue color of the surface material 2 is excessively pale and the effects of the present invention can be scarcely exerted, whereas if it exceeds 3,000 ppm, the blue color of the surface material 2 is too deep and the absorber 4 viewed through the surface material 2 sometimes does not look clean.

The method for controlling the strength of blue color of the surface material 2 includes a method of controlling the amount of the blue pigment attached to the constituent fiber of the surface material 2, a method of causing a blue pigment and a pigment except for blue color (for example, a white pigment) to attach to and/or be contained in the constituent fiber of the surface material 2 and controlling the ratio of blue pigment to the entire pigment or the total amount of pigments, and a method of producing a nonwoven fabric by combining a fiber colored blue and a fiber uncolored in blue (for example, a white fiber) and at this time, controlling the ratio of the blue-colored fiber.

In the case of coloring the constituent fiber of the surface material 2 in light blue by combining a blue pigment and a white pigment, the white pigment is preferably titanium oxide, barium sulfate, calcium carbonate, zinc oxide, silica, mica, talc or the like. The weight ratio of the white pigment is preferably from 0.1 to 20%. Specifically, if the weight ratio is less than 0.1%, light transparency is increased and the masking effect is not brought out, failing in making the yellow tint invisible, whereas if it exceeds 20%, the fiber strength is seriously impaired and productivity disadvantageously decreases when spinning the raw cotton.

Other than the pigments described above, faint blue may be displayed by using and coating a dye on the surface material 2 or coloring the adhesive or pressure-sensitive adhesive used for laminating together respective members of the absorbent article.

The nonwoven fabric of the surface material 2 has light transparency, and the light transmittance of this nonwoven fabric is preferably from 30 to 70%. If the light transmittance of the nonwoven fabric is less than 30%, the tint of the absorber may be made invisible but the liquid permeability becomes low, whereas if it exceeds 70%, the effect of blue color of the surface material 2 may not be obtained. The "light transmittance" as used herein indicates a value obtained by dividing the intensity of light that passes through the nonwoven fabric by the intensity of light that fails in passing through the nonwoven fabric, and expressed as a percentage. The light transmittance can be measured, for example, by using a flicker photometric calorimeter, "300A", manufactured by Nippon Denshoku Industries Co., Ltd.

When the absorber 4 is covered with the surface material 2, the color of the absorber 4 viewed through the surface material 2 preferably has an L* value of 88 or more, an a* value of −1 to 0.2 and a b* value of −8 to 1 in the L*a*b* color system. If the L* value is less than 88, the absorber 4 looks darkish and the user may not feel that the sanitary napkin 1 is clean. Also, if the a* value is less than −1, the absorber 4 looks green to the user, whereas if it exceeds 0.2, the color of the surface material 2 looks violet. In both cases, the sanitary napkin 1 hardly looks clean. Furthermore, if the b* value is less than −8, the blue color of the absorber 4 becomes too deep and looks darkish, whereas if the b* value exceeds 1, the absorber 4 looks yellow-tinged. In both cases, the user may not feel that the sanitary napkin 1 is clean.

In the above-described one embodiment, a sanitary napkin is described, but the present invention is not limited to a sanitary napkin. For example, in the case where the absorber of a pantiliner is tinged with yellow, the cleanliness of the pantiliner can be increased by covering the absorber of the pantiliner with a surface material colored faint blue. Furthermore, in the case of a diaper having a liquid-permeable surface sheet, a liquid-impermeable leakage-preventive sheet 3 and an absorbent core as a liquid-retentive absorber disposed to intervene therebetween, when the absorbent core is tinged with yellow, the sheet colored faint blue of the present invention can be applied to the surface sheet. In addition, the present invention can be applied to a vaginal discharge sheet, an incontinence pad and the like.

EXAMPLES

The present invention is described in greater detail below by referring to Examples. The present invention should not be construed as being limited to these Examples.

Example 1

In Example 1, a nonwoven fabric colored faint blue was produced, a yellow-tinged absorber was covered with the nonwoven fabric colored faint blue, and the color of the absorber externally viewed through the nonwoven fabric colored light blue was measured. Specifically, the colored nonwoven fabric was placed over the absorber, and the apparent color of the absorber was measured using a colorimeter from above the nonwoven fabric. By this measurement, the absorber 4 can simulate the color when the user views the absorber 4 through the surface material 2, and the color thereof can be measured.

Production of Nonwoven Fabric Colored Blue

In an HDPE/PET core-sheath composite fiber (fineness: 2.2 dtex, core-sheath ratio: 54:46 (by weight), fiber length: 51 mm), 3 wt % of titanium oxide was incorporated into the core and 4,740 ppm of Pigment Blue 29 ($SiO_2$: 39.60%, $Al_2O_3$: 23.76%, $Fe_2O_3$: 0.45%, S: 12.08%, Na: 22.59%, others: 1.52%) was incorporated into the core, whereby the HDPE/PET core-sheath composite fiber was colored blue. After the production of the nonwoven fabric, the weight ratio of the colorant was measured by the ICP-AES method using Model ICPS-8100 manufactured by Shimadzu Corp. for Si, Al and Fe and using Model IRIS Advantage manufactured by Nippon Jarrell-Ash Co. Ltd. for S and Na, as a result, the weight ratio of the colorant was 2,560 ppm based on the nonwoven fabric. Using the raw cotton of this colored composite fiber, a nonwoven fabric as a flat sheet colored blue (Nonwoven Fabric A) was produced by an air-through method using a card web. Specifically, a card web using the colorant-containing composite fiber as the binder fiber was placed on a breathable supporting member having a mesh diameter of 20 to 40 meshes and moved at a line speed of 10 m/min, and the composite fibers were bonded to each other by passing hot air at 140° C. (20 seconds) (thermal bonding system) to produce a nonwoven fabric. The basis weight of Nonwoven Fabric A produced was 30 g/m$^2$, the thickness was 1.64 mm, and the density was 0.018 g/cm$^3$.

Production of White Nonwoven Fabric

As a comparative example for Nonwoven Fabric A, a white nonwoven fabric (Comparative Example A) was produced. The production method of Comparative Example A was the same as that of Nonwoven Fabric A, except for not coloring the fiber in blue. The basis weight of Comparative Example A produced was 30 g/m$^2$, the thickness was 1.48 mm, and the density was 0.020 g/cm$^3$.

Measurement of Color of Blue-Colored Nonwoven Fabric and White Nonwoven Fabric

The color of Nonwoven Fabric A colored blue and the color of Comparative Example A that is a white nonwoven fabric were measured using a colorimeter, CR-300, manufactured by Konica Minolta. After correcting the colorimeter by using a standard white plate (L* value: 96.82, a* value: 0.45, b* value: 2.14), the standard white plate was placed below the nonwoven fabric, and the color of two kinds of nonwoven fabrics above was measured. The results expressed by the L*a*b* color system are shown in Table 1 below.

TABLE 1

Measurement Results of L*a*b* Color System for Color of Nonwoven Fabric

| | L* Value | a* Value | b* Value |
|---|---|---|---|
| Nonwoven Fabric A (blue) | 89.04 | 0.20 | −7.73 |
| Comparative Example A (white) | 95.39 | 0.25 | 2.01 |

The L* value of Nonwoven Fabric A was 89.04, and the L* value close to 100 and being 88 or more reveals that the color of Nonwoven Fabric A is a very bright color, that is, an undarkened color fairly close to white. Nonwoven Fabric A looks black when the L* value is 0, and looks white when 100. The a* value of Nonwoven Fabric A was 0.20 and is a value in the vicinity of 0, and this reveals that Nonwoven Fabric A is not tinged with red or green. Nonwoven Fabric A looks green when the a* value is −60, looks red when 60, and looks pale when the a* value is a value in the vicinity of 0. Also, the b* value of Nonwoven Fabric A was −7.73, and this reveals that Nonwoven Fabric A is tinged with faint blue. Nonwoven Fabric A looks blue when the b* value is −60, looks yellow when 60, and looks pale when the b* value is in the vicinity of 0. As the b* value of Nonwoven Fabric A comes close to 0 from −60, the color of Nonwoven Fabric A turns from deep blue into light blue. These a* value and b* value of Nonwoven Fabric A are indicating that the color of Nonwoven Fabric A is blue. Accordingly, the values in the L*a*b* color system of Nonwoven Fabric A indicate that the color of Nonwoven Fabric A is a light blue color fairly close to white, i.e., light blue.

The L* value of Comparative Example A was 95.39 and since the L* value is very close to 100, the L* value of Comparative Example A reveals that the color of Comparative Example A is white. The a* value of Comparative Example A was 0.25 and is a value in the vicinity of 0, and this reveals that Comparative Example A is not tinged with red or green. Also, the b* value of Comparative Example A was 2.01, and this reveals that Comparative Example A is tinged with yellow. These a* value and b* value of Comparative Example A are indicating that the color of Comparative Example A is faint yellow. Accordingly, the values in the L*a*b* color system of Comparative Example A indicate that the color of Comparative Example A is yellow-tinged white.

Measurement of Transmittance of Blue-Colored Light Nonwoven Fabric and White Nonwoven Fabric Blue-colored Nonwoven Fabric A and white Comparative Example A were measured for the light transmittance by using a flicker photometric calorimeter, "300A", manufactured by Nippon Denshoku Industries Co., Ltd. The light transmittance of Nonwoven Fabric A was 51.01%, and the light transmittance of Comparative Example A was 59.23%. If the light transmittance is less than 30%, the tint of the absorber may be made invisible but the liquid permeability becomes low, whereas if the light transmittance exceeds 70%, the tint of the absorber is displayed as it is.

Measurement of Color of Absorber

To confirm whether the absorber used in this Example is tinged with yellow, the color of the absorber was measured. The color of the absorber was measured using a colorimeter, CR-300, manufactured by Konica Minolta in the same manner as in the measurement of the color of nonwoven fabric. After correcting the colorimeter by using a standard white plate, the color of the absorber was measured. The absorbers measured were "tissue paper" (basis weight: 14 g/m$^2$) (hereinafter referred to as "Absorber A"), a product of RAYONIER PERFORMANCE FIBERS, which is disintegrated by a disintegrator (basis weight: 400 g/m$^2$) (hereinafter referred to as "Absorber B"), a product of Weyerhaeuser Company, which is disintegrated by a disintegrator (basis weight: 400 g/m$^2$) (hereinafter referred to as "Absorber C"), "Airlaid Pulp" produced by Oji Kinocloth Co., Ltd. (basis weight: 60 g/m$^2$) (hereinafter referred to as "Absorber D"), "Lanseal" (registered trademark), produced by Toyobo Co., Ltd. (basis weight: 100 g/m$^2$) (hereinafter referred to as "Absorber E"), and an absorber (basis weight: 400 g/m$^2$) used in "Pampers" (registered trademark) (pants type, size L) produced by Procter & Gamble Japan (hereinafter referred to as "Absorber F"). The measurement results of Absorbers A to F expressed by the L*a*b* color system are shown in Table 2 below.

TABLE 2

Measurement Results of L*a*b* Color System for Color of Each Absorber

|  | L* Value | a* Value | b* Value |
| --- | --- | --- | --- |
| Absorber A | 96.76 | 0.41 | 2.67 |
| Absorber B | 94.68 | −0.60 | 2.83 |
| Absorber C | 94.47 | −0.51 | 3.11 |
| Absorber D | 96.10 | −0.01 | 4.18 |
| Absorber E | 92.37 | −0.83 | 7.10 |
| Absorber F | 90.71 | −1.27 | 10.69 |

The L* value of Absorbers A to F was a value close to 100, and the values in Table 2 reveal that the color of Absorbers A to F is a color close to white. The a* value of Absorbers A to F was a value in the vicinity of 0, and this reveals that Absorbers A to F are not tinged with red or green. Also, the b* value of Absorbers A to F was from 2.67 to 10.69, and this reveals that Absorbers A to F are tinged with yellow. The a* value and b* value of Absorbers A to F indicate that the color of Absorbers A to F is yellow. Accordingly, the values in the L*a*b* color system of Absorbers A to F indicate that the color of Absorbers A to F is a yellow color close to yellow-tinged white. From these results, it can be confirmed that Absorbers A to F used in this Example are tinged with yellow.

Measurement of Apparent Color of Absorber when Covered with Nonwoven Fabric

The apparent color of Absorbers A to F when covered with Nonwoven Fabric A or Comparative Example A was measured using a colorimeter, CR-300, manufactured by Konica Minolta. After correcting the colorimeter by using a standard white plate, the color of Absorbers A to F was measured from above Nonwoven Fabric A or Comparative Example A covering Absorbers A to F. The measurement results expressed by the L*a*b* color system are shown in Table 3 below.

TABLE 3

Measurement Results of L*a*b* Color System for Color of Absorber When Covered with Nonwoven Fabric A or Comparative Example A

|  | Surface Material | L* Value | a* Value | b* Value |
| --- | --- | --- | --- | --- |
| Absorber A | Nonwoven Fabric A | 89.50 | 0.13 | −6.48 |
|  | Comparative Example A | 95.17 | 0.18 | 1.79 |
| Absorber B | Nonwoven Fabric A | 89.27 | −0.57 | −5.53 |
|  | Comparative Example A | 94.27 | −0.42 | 2.37 |
| Absorber C | Nonwoven Fabric A | 88.51 | −0.59 | −6.12 |
|  | Comparative Example A | 94.53 | −0.48 | 2.18 |
| Absorber D | Nonwoven Fabric A | 88.92 | −0.24 | −4.75 |
|  | Comparative Example A | 94.63 | −0.09 | 2.76 |
| Absorber E | Nonwoven Fabric A | 85.78 | −0.91 | −3.57 |
|  | Comparative Example A | 90.87 | −0.51 | 4.14 |
| Absorber F | Nonwoven Fabric A | 85.74 | −1.05 | −1.11 |
|  | Comparative Example A | 92.23 | −0.29 | 7.42 |

Absorbers A to F were covered with Nonwoven Fabric A and the apparent color of Absorbers A to F was measured using the colorimeter from above the nonwoven fabric, as a result, the b* value of Absorbers A to F was from −6.48 to −1.11. This reveals that each of Absorbers A to F when covered with Nonwoven Fabric A does not look yellow-tinged. On the other hand, when Absorbers A to F were covered with Comparative Example A and the apparent color of the absorber was measured using the colorimeter from above the nonwoven fabric, the b* value of Absorbers A to F was from 1.79 to 7.42. This reveals that even when covered with Comparative Example A, each of Absorbers A to F looks yellow-tinged.

When Nonwoven Fabric A was put over Absorbers A to F, all of Absorbers A to D showed an apparent L* value of 88 or more. This indicates that even when Absorbers A to D are covered with Nonwoven Fabric A, each of Absorbers A to D does not appear darkened in color. As for Absorbers E and F, when Nonwoven Fabric A was put over the absorber, Absorbers E and F could be made to show a b* value of 1 or less and prevented from looking yellow-tinged, but the L* value became 88 or less and this reveals that each of Absorbers E and F appears darkened in color. Accordingly, it was found that Nonwoven Fabric A can cause Absorbers A to D to look clean by covering Absorbers A to D with Nonwoven Fabric A. On the other hand, Absorbers E and F where the b* value of the absorber alone is 7.1 or more and the L* value is 92.37 or less are unsuitable for the one embodiment of the present invention, because the absorber can be prevented from looking yellow-tinged but looks darkish.

Example 2

In Example 2, the effect of decreasing the yellow tint of the absorber 4 by the surface material 2 colored light blue was confirmed by further varying the ratio of the colorant (pigment).

Production of Nonwoven Fabric Colored Blue

In an HDPE/PET core-sheath composite fiber (fineness: 2.2 dtex, core-sheath ratio: 54:46, fiber length: 51 mm), 3 wt % of titanium oxide was incorporated into the core and Pigment Blue 29 ($SiO_2$: 39.60%, $Al_2O_3$: 23.76%, $Fe_2O_3$: 0.45%, S: 12.08%, Na: 22.59%, others: 1.52%) was incorporated into the core in an amount of 1,180 ppm, 2,370 ppm or 3,555 ppm, whereby the HDPE/PET core-sheath composite fiber was colored blue to produce Nonwoven Fabrics B to D. The content of Pigment Blue 29 was 1,180 ppm in the core of the HDPE/PET composite fiber for Nonwoven Fabric B, 2,370 ppm for Nonwoven Fabric C, and 3,555 ppm for Nonwoven Fabric D. After the production of the nonwoven fabric, the weight ratio of the colorant was measured by the ICP-AES method using Model ICPS-8100 manufactured by Shimadzu Corp. for Si, Al and Fe and using Model IRIS Advantage manufactured by Nippon Jarrell-Ash Co. Ltd. for S and Na, as a result, the weight ratio of the colorant was 640 ppm based on the nonwoven fabric, in the composite fiber of Nonwoven Fabric B, 1,280 ppm based on the nonwoven fabric, in the composite fiber of Nonwoven Fabric C, and 1,920 ppm based on the nonwoven fabric, in the composite fiber of Nonwoven Fabric D. Using the raw cotton of this colored composite fiber, Nonwoven Fabrics B to D colored blue, which are Examples of the present invention, were produced in the same manner as in Example 1. The basis weight of Nonwoven Fabric B was 30 $g/m^2$, the thickness was 1.54 mm, and the density was 0.019 $g/cm^3$. The basis weight of Nonwoven Fabric C was 30 $g/m^2$, the thickness was 1.9 mm, and the density was 0.016 $g/cm^3$. The basis weight of Nonwoven Fabric D was 30 $g/m^2$, the thickness was 1.78 mm, and the density was 0.017 $g/cm^3$.

Measurement of Color of Blue-Colored Nonwoven Fabric

The color of Nonwoven Fabrics B to D colored blue was measured using a colorimeter, CR-300, manufactured by Konica Minolta. Similarly to Example 1, after correcting the colorimeter by using a standard white plate, the standard white plate was placed below Nonwoven Fabric B to D, and the color of two kinds of nonwoven fabrics above was measured. The results expressed by the L*a*b* color system are shown in Table 4 below.

TABLE 4

Measurement Results of L*a*b* Color System for Color of Nonwoven Fabric

|  | L* Value | a* Value | b* Value |
|---|---|---|---|
| Nonwoven Fabric B (640 ppm) | 93.51 | 0.21 | −0.50 |
| Nonwoven Fabric C (1280 ppm) | 92.02 | 0.16 | −2.77 |
| Nonwoven Fabric D (1920 ppm) | 90.87 | 0.20 | −4.76 |

The L* value of Nonwoven Fabrics B to D showed a value close to 100, and this reveals that the color of Nonwoven Fabrics B to D is a very bright color, that is, a color close to white. The a* value of Nonwoven Fabrics B to D was from 0.16 to 0.21 and is a value in the vicinity of 0, and this reveals that Nonwoven Fabrics B to D are not tinged with red or green. Also, the b* value of Nonwoven Fabrics B to D was from −0.5 to −4.76, and this reveals that as the content of the colorant in Nonwoven Fabrics B to D is decreased, the nonwoven fabric looks more light blue. These results indicate that the color of Nonwoven Fabrics B to D is light blue and is whitish.

Measurement of Transmittance of Blue-Colored Light Nonwoven Fabric

Nonwoven Fabrics B to D were measured for the light transmittance by using a flicker photometric calorimeter, "300A", manufactured by Nippon Denshoku Industries Co., Ltd. The light transmittance of Nonwoven Fabric B was 66.9%, the light transmittance of Nonwoven Fabric C was 61.81%, and the light transmittance of Nonwoven Fabric D was 56.88%. If the light transmittance of the nonwoven fabric is less than 30%, the tint of the absorber may be made invisible but the liquid permeability becomes bad, whereas if the light transmittance of the nonwoven fabric exceeds 70%, the tint of the absorber is displayed as it is.

Measurement of Color of Absorber when Covered with Nonwoven Fabric

The apparent color of Absorbers A to F when covered with each of Nonwoven Fabrics B to D was measured using a colorimeter, CR-300, manufactured by Konica Minolta. Absorbers A to F are the same as those in Example 1. After correcting the colorimeter by using a standard white plate, the color of Absorbers A to F was measured from above each of Nonwoven Fabrics B to D covering Absorbers A to F. The measurement results expressed by the L*a*b* color system are shown in Table 5 below. For reference, the L* value, the a* value and b* value of Nonwoven Fabric A of Example 1 are also shown in Table 5.

TABLE 5

Measurement Results of L*a*b* Color System for Color of Absorber When Covered with Nonwoven Fabrics A to D

| Surface Material | Absorber | L* Value | a* Value | b* Value |
|---|---|---|---|---|
| Nonwoven Fabric B (640 ppm) | Absorber A (L* value: 2.67) | 93.31 | 0.12 | −0.41 |
| | Absorber B (L* value: 2.83) | 93.03 | −0.57 | 0.60 |
| | Absorber C (L* value: 3.11) | 93.20 | −0.49 | 0.93 |
| | Absorber D (L* value: 4.18) | 92.26 | −0.23 | 0.43 |
| | Absorber E (L* value: 7.10) | 88.65 | −0.57 | 2.06 |
| | Absorber F (L* value: 10.69) | 88.88 | −0.59 | 2.72 |
| Nonwoven Fabric C (1280 ppm) | Absorber A (L* value: 2.67) | 91.82 | 0.08 | −2.67 |
| | Absorber B (L* value: 2.83) | 92.32 | −0.62 | −1.53 |
| | Absorber C (L* value: 3.11) | 92.29 | −0.56 | −1.41 |
| | Absorber D (L* value: 4.18) | 90.99 | −0.25 | −1.56 |
| | Absorber E (L* value: 7.10) | 88.74 | −0.81 | 1.02 |
| | Absorber F (L* value: 10.69) | 89.19 | −0.91 | 3.85 |
| Nonwoven Fabric D (1920 ppm) | Absorber A (L* value: 2.67) | 90.12 | 0.06 | −5.48 |
| | Absorber B (L* value: 2.83) | 90.39 | −0.73 | −4.01 |
| | Absorber C (L* value: 3.11) | 90.56 | −0.60 | −3.54 |
| | Absorber D (L* value: 4.18) | 88.64 | −0.30 | −4.62 |
| | Absorber E (L* value: 7.10) | 87.20 | −0.89 | −1.35 |
| | Absorber F (L* value: 10.69) | 87.26 | −1.03 | 0.49 |
| (Reference) Nonwoven Fabric A (2560 ppm) | Absorber A (L* value: 2.67) | 89.5 | 0.13 | −6.48 |
| | Absorber B (L* value: 2.83) | 89.27 | −0.57 | −5.53 |
| | Absorber C (L* value: 3.11) | 88.51 | −0.59 | −6.12 |
| | Absorber D (L* value: 4.18) | 88.92 | −0.24 | −4.75 |
| | Absorber E (L* value: 7.10) | 85.78 | −0.91 | −3.57 |
| | Absorber F (L* value: 10.69) | 85.74 | −1.05 | −1.11 |

As seen from the results in Table 5, with respect to the yellow-tinged absorber (Absorbers A to D) having a b* value of 4.18 or less, Nonwoven Fabrics B to D could make the absorber show a b* value of 1 or less and at the same time, an L* value of 88 or more. That is, the absorber can be prevented from looking yellow-tinged and darkish. Also, similarly to Nonwoven Fabric A, with respect to Absorbers E and F where the absorber alone has a b* value of 7.1 or more and an L* value of 92.37 or less, although the absorber could be prevented from looking yellow-tinged, Absorbers E and F looked darkish (when Nonwoven Fabric A or D and Absorber E or F are combined), or the absorber was prevented from looking darkish but looked yellow-tinged (when Nonwoven Fabric B or C and Absorber E or F are combined). Therefore, Absorbers E and F are found to be unsuitable for the one embodiment of the present invention.

In the case of covering Absorbers A to F with Nonwoven Fabrics B to D, the apparent a* value of Absorbers A to F was from 0.12 to −1.03. Thus, Nonwoven Fabrics B to D could prevent Absorbers A to F covered with Nonwoven Fabrics B to D from looking green or violet.

In this way, with respect to the absorber, except for the absorber where the b* value of the absorber alone is more than 5 and the L* value is less than 93, i.e., with respect to the absorber where the b* value of the absorber alone is 5 or less and the L* value is 93 or more, Nonwoven Fabrics B to D can prevent the absorber from looking yellow-tinged and darkish and can give a clean feeling to the user. More preferably, Nonwoven Absorbers B to D can prevent the absorber where the b* value of the absorber alone is 4.18 or less and the L* value is 94.47 or more, from looking yellow-tinged and darkish and can give a clean feeling to the user.

Others

Regarding the embodiment of the present invention, other mentionable points are described below.

(1) As for Fiber

The fiber orientation of the card web is directed mainly in the plane direction and in the case of a two-dimensional shape, bulk is scarcely developed. Therefore, a three-dimensional crimp shape is preferably formed so as to create a structure where bulk is developed in the thickness direction and thanks to buckling strength acting in the thickness direction, the bulk is hardly crushed even if an external pressure is applied. The three-dimensional crimp shape means, for example, a spiral, zigzag or Ω-shaped fiber. Although the fiber orientation is mainly directed in the plane direction, the fiber orientation is partially directed in the thickness direction. Because of this, the buckling strength of the fibers acts in the thickness direction, and therefore the bulk does not become flattened even if external pressure is applied. Above all, the spiral shape can return to its original shape when external pressure is released, and therefore even if the bulk is slightly crushed due to excessive external pressure, the original thickness is easily recovered after the external pressure is released. Specifically, the latent crimp fiber includes, for example, a side-by-side fiber using a polypropylene/polyolefin polypropylene copolymer. The core of the core-sheath type apparent crimp fiber is an eccentric core, and has a structure which does not become flattened, so that the bulk of the sheet is maintained. Therefore, the liquid permeability of the sheet is not lowered, liquid does not remain in the sheet, and the concealing effect of blue does not decrease. If a liquid is pooled in the sheet, the concealing effect by blue, specifically, the effect achieved by coloring blue, is reduced due to staining by the color of body fluid.

The spiral, zigzag or Ω-shaped three-dimensional structure can be made easily maintained by applying an annealing treatment to the fiber (in the case of a core-sheath composite fiber, by heat-treating the fiber at a temperature close to the melting point of the sheath component so as to stabilize the fiber shape), and bulk can be developed in the thickness direction to improve the bulk maintaining property by imparting a three-dimensional structure to fibers aligned mainly in the plane direction (see, for example, Kokai No. 2009-30218). In the embodiment of the present invention, a structure of the sheet is not easily flattened, and the bulk of the sheet is easily maintained. Therefore, the liquid permeability of the sheet is not lowered, liquid does not remain in the sheet, and the concealing effect of blue does not decrease. If a liquid is pooled in the sheet, the concealing effect by blue, specifically, the effect achieved by coloring blue, is reduced due to staining by the color of body fluid.

(2) Bulk Recovery of Nonwoven Fabric

As for the method to recover the bulk of the nonwoven fabric, which can easily recover the thickness of the nonwoven fabric reduced in the bulk due to winding, the bulk can be recovered by blowing hot air at a temperature lower than the melting point of the thermoplastic fiber. By recovering the bulk in such a way, the liquid permeability is improved because of reduction in the density of the sheet or action of raising the fiber. In the embodiment of the present invention, by virtue of good liquid permeability, liquid does not remain in the sheet and the concealing effect of blue is not reduced. If a liquid is pooled in the sheet, the concealing effect of blue, specifically, the effect achieved by coloring blue, is reduced due to staining by the color of body fluid.

(3) Regarding Density Gradient and Hydrophilicity Gradient

With respect to the sheet configuration of the absorbent article, the fiber density gradient from the surface material to the absorber is set to surface material<absorber (the fiber density of the absorber is higher than the fiber density of the surface material) and similarly, the hydrophilicity gradient is set to surface material<absorber (the hydrophilicity of the absorber is higher than the hydrophilicity of the surface material). In the embodiment of the present invention, as the result of good liquid permeability of the sheet, liquid is not allowed to remain in the sheet and reduction in the effect of the sheet colored light blue does not occur.

(4) Coloring Material Species

As the colorant for the nonwoven fabric, a fluorescent brightening agent may also be used. The fluorescent brightening agent is a dye of absorbing an ultraviolet ray and emitting blue-violet to blue-green reflected light. In this case, the nonwoven fabric tinged with blue obscures the yellowish absorber yellowing by yellow, without bringing out reduction in the brightness, since blue is the complementary color of yellow.

(5) Structure as Surface Material

Out of acute intersection angles inclusive of 90° and obtuse intersection angles larger than 90° at the intersection with a line perpendicular to the horizontal plane, the average fiber angle that is an average of acute intersection angles is set to 75° or less (see, for example, Kokai No. 2009-30218). In the embodiment of the present invention, the liquid permeation resistance is reduced and a structure of the sheet where a liquid does not remain is configured, whereby the effect of the sheet colored light blue can be prevented from being impaired.

The sanitary napkin 1 according to one embodiment described above provides the following operational effects.

(1) In a napkin 1 comprising an absorber 4 capable of absorbing a body fluid of the user, a surface material 2 covering one surface of the absorber 4 and allowing a body fluid of the user to pass through, and a leakage-preventive sheet 3 covering another surface of the absorber 4 and disallowing a body fluid of the user to pass through, a surface material 2 having an L* value of 88 or more, an a* value of 0 to 0.3 and a b* value of −8 to 0 in the L*a*b* color system is disposed to cover an absorber 4 having a b* value of 1 to 5 and an L* value of 93 or more in the L*a*b* color system, whereby the absorber 4 is prevented from looking yellow-tinged and darkish. According to the invention, when the user views a yellow-tinged absorber 4 though the surface material 2, the absorber 4 does not look yellowish and the sanitary napkin 1 looks clean.

(2) The L* value of the color of the absorber 4 when the absorber 4 is viewed through the surface material 2 is set to be 88 or more. According to the invention, when the absorber 4 is covered with the surface material 2, the absorber 4 is prevented from looking darkish. Accordingly, the absorbent article 1 can further look clean.

(3) The a* value of the color of the absorber 4 when the absorber 4 is viewed through the surface material 2 is set to be from −1 to 0.2 and the b* value is set to be from −8 to 1. Thanks to this configuration, the absorber 4 can be prevented from looking green or violet when the absorber 4 is covered with the surface material 2, and the absorbent article 1 can further look clean.

(4) A colored sheet is used for the surface material coming into contact with skin of the user. According to the invention, a sheet having a function of providing the user with good feel when the user's skin touches the absorbent article 1, and a sheet having a function of causing the absorber 4 to look clean can be configured of one sheet, and the structure of the absorbent article 1 can be made simple.

(5) The light transmittance of the surface material 2 is set to be from 30 to 70%. If the light transmittance of the nonwoven fabric is less than 30%, the tint of the absorber may be made invisible but the liquid permeability of the nonwoven fabric becomes bad, whereas if it exceeds 70%, the effect of blue color of the surface material 2 is not sufficiently exerted. In this regard, the surface material 2 can also have an effect of suppressing the yellow tint of the absorber 4 without impairing the liquid permeability as an absorbent article.

(6) The color of the surface material 2 is set to be blue, and the weight ratio of Pigment Blue 29 for coloring surface material 2 in blue is set to be from 500 to 3,000 ppm based on surface material 2, whereby the depth of the blue of the surface material 2 can be controlled such that the absorbent article 1 looks clean.

The sanitary napkin 1 according to one embodiment above can be modified as follows.

(1) The sheet whose color has an L* value of 88 or more, an a* value of 0 to 0.3 and a b* value of −7 to 0 is not limited to the surface material 2 as long as it is a liquid-permeable sheet covering one surface of the absorber 4. For example, in the case of having an intermediate sheet between the surface material and the absorber, the color of the intermediate sheet may be set to have an L* value of 88 or more, an a* value of 0 to 0.3 and a b* value of −8 to 0. Although there is not an effect that a sheet having a function of providing the user with a good feel when the user's skin touches the absorbent article and a sheet having a function of making the absorber 4 look clean can be configured of one sheet and the structure of the absorbent article 1 can be made simple, also in this case, when the user views the yellow-tinged absorber through the surface material and the intermediate sheet, the absorber can be prevented from looking yellow-tinged and the sanitary napkin looks clean. Another sheet may be disposed between the sheet whose color has an L* value of 88 or more, an a* value of 0 to 0.3 and a b* value of −8 to 0, and the absorber. That is, the sheet having the color above may cover the absorber directly or indirectly as long as it covers the absorber. Also, the sheet may cover the entire surface of the absorber or may cover a part of the surface, as long as it covers the absorber.

(2) The colorant added to have a weight ratio of 500 to 3,000 ppm based on surface material is not limited to Pigment Blue 29. The colorant may be, for example, an inorganic blue pigment such as Pigment Blue 27 and Pigment Blue 28, or an organic blue pigment such as Pigment Blue 15, Pigment Blue 16, Pigment Blue 60 and Phthalocyanine Blue α. Also in this case, the depth of blue color of the surface material can be adjusted to an optimal depth (light blue) enabling absorbent article to look clean.

(3) The sheet is not limited to nonwoven fabric as long as it is a liquid permeable sheet whose color has an L* value of 88 or more, an a* value of 0 to 0.3 and a b* value of −8 to 0. For example, the sheet may be a fiber knitted sheet.

(4) The absorbent article applied to the present invention is not limited to a sanitary napkin. The present invention can also be applied to, for example, panty liner, an incontinence pad and disposable diaper.

The embodiment may be combined with one modification example or a plurality of modification examples. It is also possible to combine modification examples with each other in any combination.

The embodiments described above are mere examples, and the present invention is not limited to these embodiments by any means.

DESCRIPTION OF NUMERICAL REFERENCES

1 Sanitary napkin
2 Surface material
3 Leakage-preventive sheet
4 Absorber

The invention claimed is:

1. An absorbent article comprising:
an absorber capable of absorbing a body fluid of a user,
a liquid-permeable sheet covering one surface of said absorber and allowing a body fluid of the user to pass through, and
a liquid-impermeable sheet covering another surface of said absorber and disallowing a body fluid of the user to pass through, wherein
the color of said liquid-permeable sheet has an L* value of 88 or more, an a* value of 0 to 0.3 and a b* value of −8 to 0 in the L*a*b* color system, and
the color of said absorber has a b* value of 1 to 5 and an L* value of 93 or more in the L*a*b* color system,
wherein said liquid permeable sheet is a nonwoven fabric comprising fibers having a three-dimensional crimp shape and having an average fiber angle of 75° or less, wherein the average fiber angle is an average value of acute intersection angles out of acute intersection angles inclusive of 90° and obtuse intersection angles larger than 90° at the intersection with a line perpendicular to the horizontal plane,
wherein the fibers have a blue tint controlled by controlling an amount of a blue pigment attached to the fibers or by causing a blue pigment and a pigment except for blue color pigment to attach to and/or be contained in the fibers, and
wherein the fibers are annealed.

2. The absorbent article as claimed in claim 1, wherein when said absorber is viewed through said liquid-permeable sheet, the L* value of the color of said absorber is 88 or more.

3. The absorbent article as claimed in claim 1, wherein when said absorber is viewed through said liquid-permeable sheet, the a* value of the color of said absorber is from −1 to 0.2 and the b* value is from −8 to 1.

4. The absorbent article as claimed in claim 1, wherein said liquid-permeable sheet is a surface material coming into contact with skin of the user or an intermediate sheet present between a surface material and said absorber.

5. The absorbent article as claimed in claim 1, wherein the light transmittance of said liquid-permeable sheet is from 30 to 70%.

6. The absorbent article as claimed in claim 1, wherein the color of said liquid-permeable sheet is blue and the weight ratio of the colorant for coloring said liquid-permeable sheet in blue is from 500 to 3,000 ppm based on said permeable sheet.

7. The absorbent article as claimed in claim 2, wherein when said absorber is viewed through said liquid-permeable sheet, the a* value of the color of said absorber is from −1 to 0.2 and the b* value is from −8 to 1.

8. The absorbent article as claimed in claim 2, wherein said liquid-permeable sheet is a surface material coming into contact with skin of the user or an intermediate sheet present between a surface material and said absorber.

9. The absorbent article as claimed in claim 3, wherein said liquid-permeable sheet is a surface material coming into contact with skin of the user or an intermediate sheet present between a surface material and said absorber.

10. The absorbent article as claimed in claim 7, wherein said liquid-permeable sheet is a surface material coming into contact with skin of the user or an intermediate sheet present between a surface material and said absorber.

11. The absorbent article as claimed in claim 2, wherein the light transmittance of said liquid-permeable sheet is from 30 to 70%.

12. The absorbent article as claimed in claim 3, wherein the light transmittance of said liquid-permeable sheet is from 30 to 70%.

13. The absorbent article as claimed in claim 4, wherein the light transmittance of said liquid-permeable sheet is from 30 to 70%.

14. The absorbent article as claimed in claim 7, wherein the light transmittance of said liquid-permeable sheet is from 30 to 70%.

15. The absorbent article as claimed in claim 8, wherein the light transmittance of said liquid-permeable sheet is from 30 to 70%.

16. The absorbent article as claimed in claim 9, wherein the light transmittance of said liquid-permeable sheet is from 30 to 70%.

17. The absorbent article as claimed in claim 10, wherein the light transmittance of said liquid-permeable sheet is from 30 to 70%.

18. The absorbent article as claimed in claim 2, wherein the color of said liquid-permeable sheet is blue and the weight ratio of the colorant for coloring said liquid-permeable sheet in blue is from 500 to 3,000 ppm based on said permeable sheet.

19. The absorbent article as claimed in claim 3, wherein the color of said liquid-permeable sheet is blue and the weight ratio of the colorant for coloring said liquid-permeable sheet in blue is from 500 to 3,000 ppm based on said permeable sheet.

20. The absorbent article as claimed in claim 4, wherein the color of said liquid-permeable sheet is blue and the weight ratio of the colorant for coloring said liquid-permeable sheet in blue is from 500 to 3,000 ppm based on said permeable sheet.

* * * * *